United States Patent [19]

Winter et al.

[11] Patent Number: 5,612,428

[45] Date of Patent: Mar. 18, 1997

[54] PROCESS FOR PREPARING OLEFIN POLYMER WITH CATALYST CONTAINING METALLOCENE

[75] Inventors: Andreas Winter, Glashütten; Frank Küber, Oberursel; Michael Aulbach, Hofheim; Bernd Bachmann, Eppstein; Robert Klein, Frankfurt am Main; Klaus Kühlein, Kelkheim; Walter Spaleck, Liederbach; Christian Kohlpaintner, Kelkheim, all of Germany

[73] Assignee: Hoechst Aktiengesellschaft, Germany

[21] Appl. No.: 477,853

[22] Filed: Jun. 7, 1995

Related U.S. Application Data

[62] Division of Ser. No. 361,762, Dec. 22, 1994.

[30] Foreign Application Priority Data

Dec. 27, 1993 [DE] Germany ............ 43 44 689.2

[51] Int. Cl.[6] .................................. C08F 4/642
[52] U.S. Cl. .................. 526/127; 526/129; 526/160; 526/943; 526/150
[58] Field of Search .................. 526/126, 127, 526/129, 160, 943

[56] References Cited

U.S. PATENT DOCUMENTS

| | | | |
|---|---|---|---|
| 5,145,819 | 9/1992 | Winter et al. | 502/117 |
| 5,243,001 | 9/1993 | Winter et al. | 526/127 |
| 5,328,969 | 7/1994 | Winter et al. | 526/127 |
| 5,329,031 | 7/1994 | Miyake et al. | 556/12 |
| 5,329,033 | 7/1994 | Spaleck et al. | 556/53 |
| 5,374,752 | 12/1994 | Winter et al. | 556/11 |

FOREIGN PATENT DOCUMENTS

| | | |
|---|---|---|
| 1317411 | 5/1993 | Canada . |
| 1319784 | 6/1993 | Canada . |
| 0302424 | 2/1989 | European Pat. Off. . |
| 0336128 | 10/1989 | European Pat. Off. . |
| 0426637 | 5/1991 | European Pat. Off. . |
| 0485822 | 5/1992 | European Pat. Off. . |
| 0524624 | 1/1993 | European Pat. Off. . |
| 0528287 | 2/1993 | European Pat. Off. . |
| 0544308 | 6/1993 | European Pat. Off. . |
| 0545303 | 6/1993 | European Pat. Off. . |
| 0574597 | 12/1993 | European Pat. Off. . |

OTHER PUBLICATIONS

X. Yang et al. (1991) J. Am. Chem. Soc. 113, 3623–3625.

J.A. Ewen et al., "Crystal Structures and Stereospecific Propylene Polymerizations with Chiral Hafnium Metallocene Catalysts" J. Am. Chem. Soc. 109 (1987) pp. 6544–6545.

H. H. Brintzinger et al., "Stereo– und Regioselektivitat von chiralen, alkylsubstituierten ansa–Zirconocen–Katalysatoren bei der Methylalumonxan–aktivierten Propen–Polymerisation" Angew. Chem. 102 (1990) pp. 339–341.

Ewen et al, "Syndiospecific Propylene Polymerizations with Group 4 Metallocenes" J. Am. Chem. Soc. 110 (1988) pp. 6255–6258.

*Primary Examiner*—Mark Nagumo
*Attorney, Agent, or Firm*—Connolly & Hutz

[57] ABSTRACT

The invention relates to a metallocene compound of the formula I

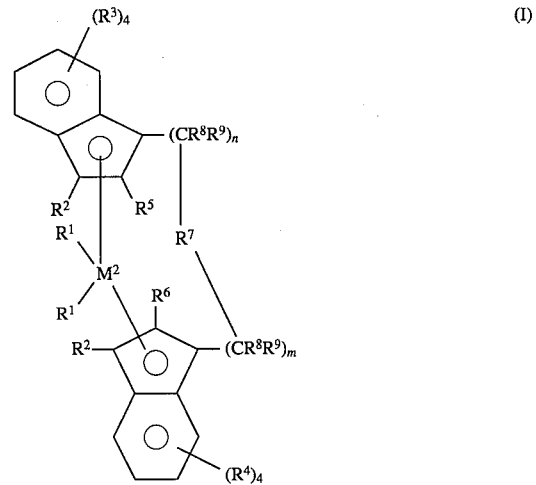

where the two indenyl ligands have substitution patterns different from one another. The metallocene compound can be used as catalyst component for olefin polymerization.

3 Claims, No Drawings

PROCESS FOR PREPARING OLEFIN POLYMER WITH CATALYST CONTAINING METALLOCENE

This application is a division of our application Ser. No. 08/361,762, filed Dec. 22, 1994, now allowed.

The invention relates to a metallocene compound which can advantageously be used at industrially relevant temperatures for preparing polyolefins having high isotacticity and high molecular weight.

The literature discloses the preparation of polyolefins using soluble metallocene compounds in combination with aluminoxanes or other cocatalysts which, owing to their Lewis acidity, can convert the neutral metallocene into a cation and stabilize it.

For example, a special preactivation method for the metallocene using an aluminoxane has been proposed, which leads to an appreciable increase in the activity of the catalyst system and to a significant improvement in the particle morphology of the polymer (cf. EP 0 302 424). Although the preactivation does increase the molecular weight, no substantial increase can be achieved.

A further, but still insufficient, increase in the molecular weight has been achieved by use of specific heteroatom-bridged metallocenes at high metallocene activity (EP-A 0 336 128).

Furthermore, catalysts based on ethylenebisindenyl-hafnium dichloride and ethylenebis (4,5,6,7-tetrahydro-1-indenyl)hafnium dichloride and methylaluminoxane are known, by means of which relatively high-molecular-weight polypropylenes can be prepared by suspension polymerization (cf. J. A. Ewen et al., *J. Am. Chem. Soc.* 109 (1987) 6544). However, under industrially relevant polymeri-zation conditions, the particle morphology of the polymers produced in this way is not satisfactory and the activity of the catalysts used is comparatively low. Combined with the high catalyst costs, an inexpensive polymerization is thus not possible using these systems.

A significant increase in the molecular weight has been achieved by the use of metallocenes in which the aromatic π ligands fixed by means of a bridge bear substituents in the 2-position (EP 485 822) or in the 2 and 4,6 positions (EP 545 303).

To meet the demands for inexpensive large-scale production, polymerization has to be carried out at reaction temperatures which are as high as possible, since at higher polymerization temperatures the heat of polymerization generated can be removed using less coolant and can therefore be achieved using a significantly smaller cooling water circuit.

In this respect, the last named metallocenes having substituents in the 2 or 4 and 6 positions to the bridge are very effective even at a polymerization temperature of 70° C., but nevertheless the achievable molecular weights at industrially relevant polymerization temperatures (e.g. 70° C.) are still too small for some industrial applications such as, for example, the production of polymers for pipes and large hollow bodies and also specific fibers.

Metallocenes having two substituted cyclopentadienyl π ligands such as, for instance, dimethylsilanediyl(2-methyl-4-t-butyl-1-cyclopentadienyl)$_2$ZrCl$_2$ have likewise been proposed as polymerization catalysts (H.-H. Brintzinger et al., Angew. Chem. 102 (1990) 339), but these systems are in no way convincing with regard to achievable polymer molecular weight, stereospecificity or polymer melting point; furthermore their polymerization activity is very low and the necessary separation of the meso and rac forms obtained from the synthesis is very difficult—isotactic polyolefin can only be prepared using the rac form. In addition, the meso form is obtained in about the same amount as the rac form, which means that half of the chemicals used have to be disposed of and only half the product is usable.

EP 544 308 proposes catalysts having two different π ligands such as, for instance, isopropylidene(4-methyl-1-cyclopentadienyl)(3-t-butyl-1-indenyl)ZrCl$_2$ which, owing to their asymmetry, have a priori no meso form and thus circumvent the rac/meso separation problem, but the deficiencies with regard to polymer properties and catalyst activity were not able to be solved.

The work of Ewen et al. (*J. Am. Chem. Soc.* 110 (1988) 6255) likewise discloses catalysts having two different π ligands such as, for instance, isopropylidene(cyclopentadienyl)(fluorenyl)ZrCl$_2$. However, these asymmetric compounds produce syndiotactic polyolefins, the preparation of isotactic polyolefins is not possible therewith.

It is thus an object of the invention to provide a catalyst system which avoids the disadvantages of the prior art and, particularly at industrially relevant polymerization temperatures, produces polyolefins having a high molecular weight at high isotactic stereoselectivity and polymerization activity.

It has been found that this object can be achieved by means of a metallocene compound having two differing indenyl ligands which are substituted in a certain manner.

Owing to their chemical structure, the metallocenes of the invention have no meso form which would have to be separated off in a complicated manner, since only atactic polyolefin can be prepared using meso forms.

Furthermore, the proposed metallocene catalyst concept makes it possible, by combination of π ligands which differ little, to provide an inexpensive-to-prepare range of polymerization catalysts for different polymerization and product requirements.

The present invention provides a metallocene compound of the formula I

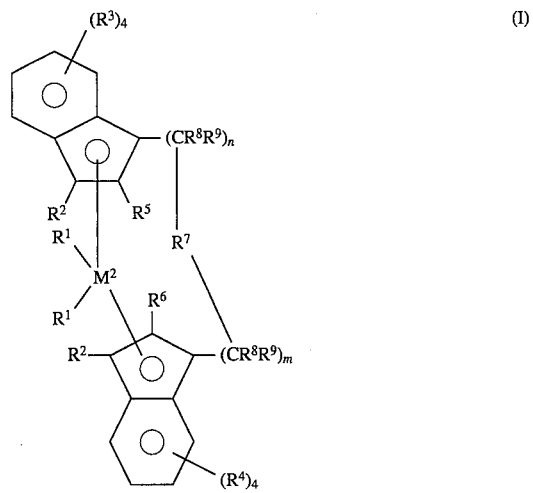

where

M$^2$ is a metal of group IVb, Vb or VIb of the Periodic Table, the radicals R$^1$ are identical or different and are a hydrogen atom, a C$_1$–C$_{10}$-alkyl group, a C$_1$–C$_{10}$-alkoxy group, a C$_6$–C$_{10}$-aryl group, a C$_6$–C$_{10}$-aryloxy group, a C$_2$–C$_{10}$-alkenyl group, a C$_7$–C$_{40}$-arylalkyl group, a C$_7$–C$_{40}$-alkylaryl group, a C$_8$–C$_{40}$-arylalkenyl group or a halogen atom, the radicals R$^2$ are identical or different and are hydrogen, a halogen atom, a C$_1$–C$_{10}$-alkyl group, which can be halogenated, a $C_6$–$C_{10}$-aryl group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$–$C_{10}$-alkyl group or a $C_6$–$C_{10}$-aryl group, the radicals $R^3$ are identical or different and are a hydrogen atom, a halogen atom, a $C_1$–$C_{20}$-alkyl group, a $C_1$–$C_{20}$-fluoroalkyl group, a $C_6$–$C_{30}$-aryl group, a $C_6$–$C_{30}$-fluoroaryl group, a $C_1$–$C_{20}$-alkoxy group, a $C_2$–$C_{20}$-alkenyl group, a $C_7$–$C_{40}$-arylalkyl group, a $C_8$–$C_{40}$-arylalkenyl group, a $C_7$–$C_{40}$-alkylaryl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$–$C_{10}$-alkyl group or a $C_6$–$C_{10}$-aryl group, or two or more radicals $R^3$ together with the atoms connecting them form a ring system, the radicals $R^4$ are identical or different and are a hydrogen atom, a halogen atom, a $C_1$–$C_{20}$-alkyl group, a $C_1$–$C_{20}$-fluoroalkyl group, a $C_6$–$C_{30}$-aryl group, a $C_6$–$C_{30}$-fluoroaryl group, a $C_1$–$C_{20}$-alkoxy group, a $C_2$–$C_{20}$-alkenyl group, a $C_7$–$C_{40}$-arylalkyl group, a $C_8$–$C_{40}$-arylalkenyl group, a $C_7$–$C_{40}$-alkylaryl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$–$C_{10}$-alkyl group or a $C_6$–$C_{10}$-aryl group, or two or more radicals $R^4$ together with the atoms connecting them form a ring system, $R^5$ is a halogen atom, a $C_1$–$C_{10}$-alkyl group, which can be halogenated, a $C_6$–$C_{10}$-aryl group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$–$C_{10}$-alkyl group or a $C_6$–$C_{10}$-aryl group, $R^6$ is a hydrogen atom, a halogen atom, a $C_1$–$C_{10}$-alkyl group, which can be halogenated, a $C_6$–$C_{10}$-aryl group, a $C_2$–$C_{10}$-alkenyl group, a $C_7$–$C_{40}$-arylalkyl group, a $C_7$–$C_{40}$-alkyloxy group, a $C_8$–$C_{40}$-arylalkenyl group, a —$NR_2^{10}$, —$OR^{10}$, —$SR^{10}$, —$OSiR_3^{10}$, —$SiR_3^{10}$ or —$PR_2^{10}$ radical, where $R^{10}$ is a halogen atom, a $C_1$–$C_{10}$-alkyl group or a $C_6$–$C_{10}$-aryl group, $R^7$ is

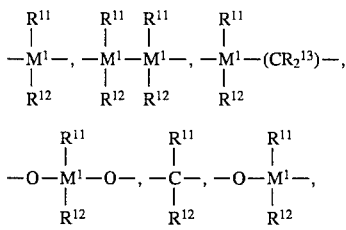

=$BR^{11}$, =$AlR^{11}$, —Ge—, —Sn—, —O—, —S—, =SO, =$SO_2$, =$NR^{11}$, =CO, =$PR^{11}$ or =$P(O)R^{11}$, where $R^{11}$, $R^{12}$ and $R^{13}$ are identical or different and are a hydrogen atom, a halogen atom, a $C_1$–$C_{20}$-alkyl group, a $C_1$–$C_{20}$-fluoroalkyl group, a $C_6$–$C_{30}$-aryl group, a $C_6$–$C_{30}$-fluoroaryl group, a $C_1$–$C_{20}$-alkoxy group, a $C_2$–$C_{20}$-alkenyl group, a $C_7$–$C_{40}$-arylalkyl group, a $C_8$–$C_{40}$-arylalkenyl group, a $C_7$–$C_{40}$-alkylaryl group, or $R^{11}$ and $R^{12}$ or $R^{11}$ and $R^{13}$ together with the atoms connecting them form a ring, $M^1$ is silicon, germanium or tin, $R^8$ and $R^9$ are identical or different and are a hydrogen atom, a halogen atom, a $C_1$–$C_{20}$-alkyl group, a $C_1$–$C_{20}$-fluoroalkyl group, a $C_6$–$C_{30}$-aryl group, a $C_6$–$C_{30}$-fluoroaryl group, a $C_1$–$C_{20}$-alkoxy group, a $C_2$–$C_{20}$-alkenyl group, a $C_7$–$C_{40}$-arylalkyl group, a $C_8$–$C_{40}$-arylalkenyl group, a $C_7$–$C_{40}$-alkylaryl group, or $R^8$ and $R^9$ together with the atoms connecting them form a ring, m and n are identical or different and are zero, 1 or 2, where m plus n is zero, 1 or 2, wherein the two indenyl ligands have substitution patterns different from one another.

Alkyl is straight-chain or branched alkyl. Halogen (halogenated) is fluorine, chlorine, bromine or iodine, preferably fluorine or chlorine. Radicals having the same indexing can be different.

$M^2$ is a metal of group IVb, Vb or VIb of the Periodic Table, for example titanium, zirconium, vanadium, niobium, tantalum, chromium, molybdenum, tungsten, preferably zirconium, hafnium, titanium, particularly preferably zirconium.

The radicals $R^1$ are identical or different, preferably identical, and are a hydrogen atom, a $C_1$–$C_{10}$—, preferably $C_1$–$C_3$-alkyl group, a $C_1$–$C_{10}$—, preferably $C_1$–$C_3$-alkoxy group, a $C_6$–$C_{10}$—, preferably $C_6$–$C_8$-aryl group, a $C_6$–$C_{10}$—, preferably $C_6$–$C_8$-aryloxy group, a $C_2$–$C_{10}$—, preferably $C_2$–$C_4$-alkenyl group, a $C_7$–$C_{40}$—, preferably $C_7$–$C_{10}$-arylalkyl group, a $C_7$–$C_{40}$, preferably $C_7$–$C_{12}$-alkylaryl group, a $C_8$–$C_{40}$—, preferably $C_8$–$C_{12}$-arylalkenyl group or a halogen atom, preferably chlorine.

The radicals $R^2$ are identical or different, preferably identical, and are a hydrogen atom, a halogen atom, preferably a fluorine, chlorine or bromine atom, a $C_1$–$C_{10}$—, preferably $C_1$–$C_4$-alkyl group, which can be halogenated, a $C_6$–$C_{10}$—, preferably $C_6$–$C_8$-aryl group, a $C_2$–$C_{10}$—, preferably $C_2$–$C_4$-alkenyl group, a $C_7$–$C_{40}$—, preferably $C_7$–$C_{40}$-arylalkyl group, a $C_7$–$C_{40}$—, preferably $C_7$–$C_{12}$-alkylaryl group, a $C_8$–$C_{40}$—, preferably $C_8$–$C_{12}$-arylalkenyl group, a —$NR_2^{10}$, —$SR^{10}$, —$OSiR_3^{10}$, —$OR^{10}$, —$SiR_3^{10}$ or —$PR_2^{10}$ radical, where $R^{10}$ is a halogen atom, preferably a chlorine atom, or a $C_1$–$C_{10}$, preferably $C_1$–$C_3$-alkyl group or a $C_6$–$C_{10}$—, preferably $C_6$–$C_8$-aryl group, particularly preferably both radicals $R^2$ are hydrogen.

The radicals $R^3$ are each identical or different and are a hydrogen atom, a halogen atom, a $C_1$–$C_{20}$—, preferably $C_1$–$C_{10}$-alkyl group, a $C_1$–$C_{20}$-fluoroalkyl group, preferably a $C_1$–$C_{10}$-fluoroalkyl group, a $C_6$–$C_{30}$—, preferably $C_6$–$C_{20}$-aryl group, a $C_6$–$C_{30}$-fluoroaryl group, preferably a $C_6$–$C_{20}$-fluoroaryl group, a $C_1$–$C_{20}$—, preferably $C_1$–$C_{10}$-alkoxy group, a $C_2$–$C_{20}$—, preferably $C_2$–$C_{10}$-alkenyl group, a $C_7$–$C_{40}$—, preferably $C_7$–$C_{20}$—arylalkyl group, a $C_8$–$C_{40}$—, preferably $C_8$–$C_{22}$-arylalkenyl group, a $C_7$–$C_{40}$—, preferably $C_7$–$C_{22}$-alkylaryl group, a —$NR_2^{10}$, —$SR^{10}$, —$OSiR_3^{10}$, —$OR^{10}$, —$SiR_3^{10}$ or —$PR_2^{10}$ radical, where $R^{10}$ is a halogen atom, preferably a chlorine atom, or a $C_1$–$C_{10}$—, preferably $C_1$–$C_3$-alkyl group or a $C_6$–$C_{10}$—, preferably $C_6$–$C_8$-aryl group, or two or more radicals $R^3$ together with the atoms connecting them form a ring system which is monocyclic or polycyclic.

The radicals $R^4$ are each identical or different and are a hydrogen atom, a halogen atom, a $C_1$–$C_{20}$—, preferably $C_1$–$C_{10}$-alkyl group, a $C_1$–$C_{20}$-fluoroalkyl group, preferably a $C_1$–$C_{10}$-fluoroalkyl group, a $C_6$–$C_{30}$—, preferably $C_6$–$C_{20}$-aryl group, a $C_6$–$C_{30}$-fluoroaryl group, preferably a $C_6$–$C_{20}$-fluoroaryl group, a $C_1$–$C_{20}$—, preferably $C_1$–$C_{10}$-alkoxy group, a $C_2$–$C_{20}$—, preferably $C_2$–$C_{10}$-alkenyl group, a $C_7$–$C_{40}$—, preferably $C_7$–$C_{20}$-arylalkyl group, a $C_8$–$C_{40}$—, preferably $C_8$–$C_{22}$-arylalkenyl group, a $C_7$–$C_{40}$—, preferably $C_7$–$C_{22}$-alkylaryl group, a —$NR_2^{10}$, —$SR^{10}$, —$OSiR_3^{10}$, —$OR^{10}$, —$SiR_3^{10}$ or —$PR_2^{10}$ radical, where $R^{10}$ is a halogen atom, preferably a chlorine atom, or a $C_1$–$C_{10}$—, preferably $C_1$–$C_3$-alkyl group or a $C_6$–$C_{10}$—, preferably $C_6$–$C_8$-aryl group, or two or more radicals $R^4$ together with the atoms connecting them form a ring system which is monocyclic or polycyclic.

$R^5$ is a halogen atom, preferably a fluorine, chlorine or bromine atom, a $C_1$–$C_{10}$—, preferably $C_1$–$C_4$-alkyl group which can be halogenated, a $C_6$–$C_{10}$—, preferably $C_6$–$C_8$-aryl group, a $C_2$–$C_{10}$—, preferably $C_2$–$C_4$-alkenyl group, a $C_7$–$C_{40}$—, preferably $C_7$–$C_{10}$-arylalkyl group, a $C_7$–$C_{40}$—, preferably $C_7$–$C_{12}$-alkylaryl group, a $C_8$–$C_{40}$—, preferably $C_8$–$C_{12}$-arylalkenyl group, a —$NR_2^{10}$, —$OSiR_3^{10}$, —$OR^{10}$, —$SiR_3^{10}$ or —$PR_2^{10}$ radical, where $R^{10}$ is a halogen atom, preferably a chlorine atom, or a $C_1$–$C_{10}$—, preferably $C_1$–$C_3$-alkyl group or a $C_6$–$C_{10}$—, preferably $C_6$–$C_8$-aryl group.

$R^6$ is a hydrogen atom, a halogen atom, preferably a fluorine, chlorine or bromine atom, a $C_1$–$C_{10}$—, preferably $C_1$–$C_4$-alkyl group which can be halogenated, a $C_6$–$C_{10}$—, preferably $C_6$–$C_8$-aryl group, a $C_2$–$C_{10}$—, preferably $C_2$–$C_4$-alkenyl group, a $C_7$–$C_{40}$—, preferably $C_7$–$C_{10}$-arylalkyl group, a $C_7$–$C_{40}$—, preferably $C_7$–$C_{12}$-alkylaryl group, a $C_8$–$C_{40}$—, preferably $C_8$–$C_{12}$-arylalkenyl a halogen atom, preferably a chlorine atom, or a $C_1$–$C_{10}$—, preferably $C_1$–$C_3$-alkyl group, a —$NR_2^{10}$, —$SR^{10}$, —$OSiR_3^{10}$, —$OR^{10}$, $SiR_3^{10}$ or —$PR_2^{10}$ radical, where $R^{10}$ is group or a $C_6$–$C_{10}$—, preferably $C_6$–$C_8$-aryl group.

$R^7$ is

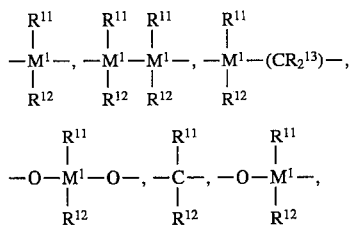

$=BR^{11}$, $=AlR^{11}$, —Ge—, —Sn—, —O—, —S—, $=SO$, $=SO_2$, $=NR^{11}$, $=CO$, $=PR^{11}$ or $=P(O)R^{11}$,
where $R^{11}$, $R^{12}$ and $R^{13}$ are identical or different and are a hydrogen atom, a halogen atom, a $C_1$–$C_{20}$—, preferably $C_1$–$C_{10}$-alkyl group, a $C_1$–$C_{20}$-fluoroalkyl group, preferably a $C_1$–$C_{10}$-fluoroalkyl group, a $C_6$–$C_{30}$—, preferably $C_6$–$C_{20}$-aryl group, a $C_6$–$C_{30}$-fluoroaryl group, preferably a $C_6$–$C_{20}$-fluoroaryl group, a $C_1$–$C_{20}$—, preferably $C_1$–$C_{10}$-alkoxy group, a $C_2$–$C_{20}$—, preferably $C_2$–$C_{10}$-alkenyl group, a $C_7$–$C_{40}$—, preferably $C_7$–$C_{20}$-arylalkyl group, a $C_8$–$C_{40}$—, preferably $C_8$–$C_{22}$-arylalkenyl group, or a $C_7$–$C_{40}$—, preferably $C_7$–$C_{22}$-alkylaryl group, or $R^{11}$ and $R^{12}$ or $R^{11}$ and $R^{13}$ together with the atoms connecting them form a ring.

$M^1$ is silicon, germanium or tin, preferably silicon and germanium.

$R^7$ is preferably $=CR^{11}R^{12}$, $=SiR^{11}R^{12}$, $=GeR^{11}R^{12}$, —O—, —S—, $=SO$, $=PR^{11}$ or $=P(O)R^{11}$.

$R^8$ and $R^9$ are identical or different and are a hydrogen atom, a halogen atom, a $C_1$–$C_{20}$—, preferably $C_1$–$C_{10}$-alkyl group, a $C_1$–$C_{20}$-fluoroalkyl group, preferably $C_1$–$C_{10}$-fluoroalkyl group, a $C_6$–$C_{30}$—, preferably $C_6$–$C_{20}$-aryl group, a $C_6$–$C_{30}$-fluoroaryl group, preferably a $C_6$–$C_{20}$-fluoroaryl group, a $C_1$–$C_{20}$—, preferably $C_1$–$C_{10}$-alkoxy group, a $C_2$–$C_{20}$—, preferably $C_2$–$C_{10}$-alkenyl group, a $C_7$–$C_{40}$—, preferably $C_7$–$C_{20}$-arylalkyl group, a $C_8$–$C_{40}$—, preferably $C_8$–$C_{22}$-arylalkenyl group or a $C_7$–$C_{40}$—, preferably $C_7$–$C_{22}$-alkylaryl group, or $R^8$ and $R^9$ together with the atoms connecting them form a ring.

m and n are identical or different and are zero, 1 or 2, preferably zero or 1, where m plus n is zero, 1 or 2, preferably zero or 1.

The two indenyl ligands have substitution patterns different from one another, particularly on the six-membered ring.

Preference is given to metallocenes of the formula I where $M^2$ is zirconium, the radicals $R^1$ are identical and are methyl or chlorine, $R^2$ is hydrogen, the radicals $R^3$ are a hydrogen atom, a $C_1$–$C_{20}$-alkyl group or a $C_6$–$C_{30}$-aryl group, or two or more radicals $R^3$ together with the atoms connecting them form a ring system, the radicals $R^4$ are a hydrogen atom, a $C_1$–$C_{20}$-alkyl group or a $C_6$–$C_{30}$-aryl group, or two or more radicals $R^4$ together with the atoms connecting them form a ring system, $R^5$ is a $C_1$–$C_{10}$, preferably $C_1$–$C_4$-alkyl group, $R^6$ is a hydrogen atom or a $C_1$–$C_{10}$—, preferably $C_1$–$C_4$-alkyl group, $R^7$ is a radical

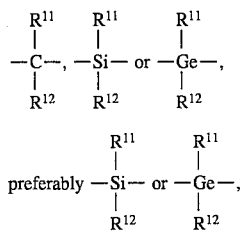

where $R^{11}$ and $R^{12}$ are identical or different and are a $C_1$–$C_{20}$-alkyl group or a $C_6$–$C_{30}$-aryl group, $R^8$ and $R^9$ are identical or different and are a hydrogen atom, a $C_1$–$C_{20}$-alkyl group or a $C_6$–$C_{30}$-aryl group, and m plus n is zero or 1, in particular those compounds of the formula I in which at least one of the two indenyl ligands has substituents which are not hydrogen in the 2, 2,4, 2,5, 2,6, 2,4,6, 2,4,5, 2,4,5,6 or 2,5,6 position.

Particularly preferred compounds of the formula I consist of the following molecule fragments a, b, c and d:

a) —$(CR^8R^9)_m$—$R^7$—$(CR^8R^9)_n$ is dialkylsilanediyl, alkyl(aryl)silanediyl, 1,2-ethanediyl, 1,2-butanediyl, diarylsilanediyl, dialkylmethylene, diarylmethylene, alkyl(aryl)methylene, alkyl(vinyl)silanediyl, aryl(vinyl)silanediyl or dialkylgermyl, b) $R^3{}_4R^2R^5$-1-indenyl is 2-alkyl-4-aryl-1-indenyl, 2,4-dialkyl-1-indenyl, 2,4,6-trialkyl-1-indenyl, 2-alkyl-4,5-benzo-1-indenyl, 2,5-dialkyl-1-indenyl, 2,5,6-trialkyl-1-indenyl, 2,4,5-trialkyl-1-indenyl, 2-alkyl-1-indenyl, 2-aryl-1-indenyl, 2,6-alkyl-4-aryl-1-indenyl, 2-alkyl-5-aryl-1-indenyl, 2-alkyl-5,6-diaryl-1-indenyl, 2-alkyl-4,5-diaryl-1-indenyl or 2-alkyl-4,6-diaryl-1-indenyl, c) $R^4{}_4R^2R^6$-1-indenyl is 2-alkyl-4-aryl-1-indenyl, 2,4-dialkyl-1-indenyl, 2,4,6-trialkyl-1-indenyl, 2-alkyl-4,5-benzo-1-indenyl, 2,5-dialkyl-1-indenyl, 2,5,6-trialkyl-1-indenyl, 2,4,5-trialkyl-1-indenyl, 2-alkyl-1-indenyl, 2-aryl-1-indenyl, 2,6-alkyl-4-aryl-1-indenyl, 2-alkyl-5-aryl-1-indenyl, 2-alkyl-5,6-diaryl-1-indenyl, 2-alkyl-4,5-diaryl-1-indenyl, 2-alkyl-4,6-diaryl-1-indenyl or 1-indenyl, d) $M^2R^1{}_2$ is $ZrCl_2$, $Zr(Me)Cl$ or $ZrMe_2$.

Examples of the compounds of the formula I are:
dimethylsilanediyl(2-methyl-4,5-benzo-1-indenyl)(2-ethyl-4-phenyl-1-indenyl)$ZrCl_2$,
dimethylsilanediyl(2,5,6-trimethyl-1-indenyl)(2-ethyl-4-phenyl-1-indenyl)$ZrCl_2$, dimethylsilanediyl(2-ethyl-1-indenyl)(1-indenyl)$ZrCl_2$,
dimethylsilanediyl(2-methyl-4,6-diisopropyl-1-indenyl)(2-methyl-4-phenyl-1-indenyl)$ZrCl_2$,
dimethylsilanediyl(2,4,6-trimethyl-1-indenyl)(2-methyl-4-phenyl-1-indenyl)$ZrCl_2$, dimethylsilanediyl(2-methyl-4-isopropyl-1-indenyl)(2-methyl-4-phenyl-1-indenyl)$ZrCl_2$,
dimethylsilanediyl(2-methyl-α-acenaphth-1-indenyl)(2-methyl-4-phenyl-1-indenyl)$ZrCl_2$, dimethylsilanediyl(2-methyl-4,5-benzo-1-indenyl)(2-methyl-4-phenyl-1-indenyl)ZrCl₂,
dimethylsilanediyl(2-methyl-5-isobutyl-1-indenyl)(2-methyl-4-phenyl-1-indenyl)ZrCl₂,
dimethylsilanediyl(2,5,6-trimethyl-1-indenyl)(2-methyl-4-phenyl-1-indenyl)ZrCl₂,
dimethylsilanediyl(4-phenyl-1-indenyl)(2-methyl-4-phenyl-1-indenyl)ZrCl₂,
dimethylsilanediyl(2-methyl-4,6-diisopropyl-1-indenyl)(2-methyl-4,5-benzo-1-indenyl)ZrCl₂,
dimethylsilanediyl(2,4,6-trimethyl-1-indenyl)(2-methyl-4,5-benzo-1-indenyl)ZrCl₂,
dimethylsilanediyl(2-methyl-4-isopropyl-1-indenyl)(2-methyl-4,5-benzo-1-indenyl)ZrCl₂,
dimethylsilanediyl(2-methyl-α-acenaphth-1-indenyl)(2-methyl-4,5-benzo-1-indenyl)ZrCl₂,
dimethylsilanediyl(4,5-benzo-1-indenyl)(2-methyl-4,5-benzo-1-indenyl)ZrCl₂,
dimethylsilanediyl(2,5,6-trimethyl-1-indenyl)(2-methyl-4,5-benzo-1-indenyl)ZrCl₂,
dimethylsilanediyl(4,6-dimethyl-1-indenyl)(2,4,6-trimethyl-1-indenyl)ZrCl₂,
dimethylsilanediyl(2-methyl-4-isopropl-1-1-indenyl)(2,4,6-trimethyl-1-indenyl)ZrCl₂,
dimethylsilanediyl(2-methyl-α-acenaphth-1-indenyl)(2,4,6-trimethyl-1-indenyl)ZrCl₂,
dimethylsilanediyl(2-methyl-4,6-diisopropyl-1-indenyl)(2,4,6-trimethyl-1-indenyl)ZrCl₂,
dimethylsilanediyl(2,5,6-trimethyl-1-indenyl)(2,4,6-trimethyl-1-indenyl)ZrCl₂,
dimethylsilanediyl(2,4,6-trimethyl-1-indenyl)(2-methyl-4,6-diisopropyl-1-indenyl)ZrCl₂,
dimethylsilanediyl(2-methyl-4-isopropyl-1-indenyl)(2-methyl-4,6-diisopropyl-1-indenyl)ZrCl₂,
dimethylsilanediyl(2-methyl-α-acenaphth-1-indenyl)(2-methyl-4,6-diisopropyl-1-indenyl)ZrCl₂,
dimethylsilanediyl(2-methyl-4-phenyl-1-indenyl)(1-indenyl)ZrCl₂,
dimethylsilanediyl(2-methyl-4-phenyl-1-indenyl)(2-methyl-1-indenyl)ZrCl₂,
dimethylsilanediyl(2-ethyl-4-phenyl-1-indenyl)(2-methyl-1-indenyl)ZrCl₂,
dimethylsilanediyl(2-methyl-4(1-naphthyl)-1-indenyl)(2-methyl-1-indenyl)ZrCl₂,
dimethylsilanediyl(2-methyl-4,6-diisopropyl-1-indenyl)(2-methyl-1-indenyl)ZrCl₂,
dimethylsilanediyl(2,4,6-trimethyl-1-indenyl)(2-methyl-1-indenyl)ZrCl₂,
dimethylsilanediyl(2-methyl-4-isopropyl-1-indenyl)(2-methyl-1-indenyl)ZrCl₂,
dimethylsilanediyl(2-methyl-α-acenaphth-1-indenyl)(2-methyl-1-indenyl)ZrCl₂,
dimethylsilanediyl(2-methyl-4,5-benzo-1-indenyl)(2-methyl-1-indenyl)ZrCl₂,
dimethylsilanediyl(2-methyl-5-isobutyl-1-indenyl)(2-methyl-1-indenyl)ZrCl₂,
dimethylsilanediyl(2,5,6-trimethyl-1-indenyl)(2-methyl-1-indenyl)ZrCl₂,
phenyl(methyl)silanediyl(2-methyl-4-phenyl-1-indenyl)(2-methyl-1-indenyl)ZrCl₂,
diphenylsilanediyl(2-methyl-4-phenyl-1-indenyl)(2-methyl-1-indenyl)ZrCl₂,
1,2-ethanediyl(2-methyl-4-phenyl-1-indenyl)(2-methyl-1-indenyl)ZrCl₂,
1,2-butanediyl(2-methyl-4-phenyl-1-indenyl)(2-methyl-1-indenyl)ZrCl₂,
dimethylgermyl(2-methyl-4-phenyl-1-indenyl)(2-methyl-1-indenyl)ZrCl₂,
methyl(vinyl)silanediyl(2-methyl-4-phenyl-1-indenyl)(2-methyl-1-indenyl)ZrCl₂,
phenyl(vinyl)silanediyl(2-methyl-4-phenyl-1-indenyl)(2-methyl-1-indenyl)ZrCl₂,
dimethylsilanediyl(2-methyl-4-phenyl-1-indenyl)(2-ethyl-4-phenyl-1-indenyl)ZrCl₂,
dimethylsilanediyl(2-methyl-4(1-naphthyl)-1-indenyl)(2-ethyl-4-phenyl-1-indenyl)ZrCl₂,
dimethylsilanediyl(2-methyl-4,6-diisopropyl-1-indenyl)(2-ethyl-4-phenyl-1-indenyl)ZrCl₂,
dimethylsilanediyl(2,4,6-trimethyl-1-indenyl)(2-ethyl-4-phenyl-1-indenyl)ZrCl₂,
dimethylsilanediyl(2-methyl-4(1-naphthyl)-1-indenyl)(2-methyl-4-phenyl-1-indenyl)ZrCl₂,
dimethylsilanediyl(2,5,6-trimethyl-1-indenyl)(2-ethyl-4-phenyl-1-indenyl)ZrCl₂,
dimethylsilanediyl(2-methyl-4-isopropyl-1-indenyl)(2-ethyl-4-phenyl-1-indenyl)ZrCl₂,
dimethylsilanediyl(α-acenaphth-1-indenyl)(2-ethyl-4-phenyl-1-indenyl)ZrCl₂,
dimethylsilanediyl(2,5,6-trimethyl-1-indenyl)(2-ethyl-4-phenyl-1-indenyl)ZrCl₂,
dimethylsilanediyl(2-methyl-4,6-diisopropyl-1-indenyl)(1-indenyl)ZrCl₂,
dimethylsilanediyl(2,4,6-trimethyl-1-indenyl)(1-indenyl)ZrCl₂,
dimethylsilanediyl(2-methyl-4-isopropyl-1-indenyl)(1-indenyl)ZrCl₂,
dimethylsilanediyl(2-methyl-4-isobutyl-1-indenyl)(1-indenyl)ZrCl₂,
dimethylsilanediyl(2,4-dimethyl-1-indenyl)(1-indenyl)ZrCl₂,
dimethylsilanediyl(2,5,6-trimethyl-1-indenyl)(1-indenyl)ZrCl₂,
dimethylsilanediyl(2-methyl-α-acenaphth-1-indenyl)(1-indenyl)ZrCl₂,
dimethylsilanediyl(2-methyl-4,5-benzo-1-indenyl)(1-indenyl)ZrCl₂,
dimethylsilanediyl(2-methyl-5-isobutyl-1-indenyl)(1-indenyl)ZrCl₂,
dimethylsilanediyl(2-ethyl-4-(1-naphthyl)-1-indenyl)(1-indenyl)ZrCl₂,
dimethylsilanediyl(2-methyl-1-indenyl)(1-indenyl)ZrCl₂,
dimethylsilanediyl(2-methyl-4-phenyl-1-indenyl)(1-indenyl)ZrCl₂,
dimethylsilanediyl(2-ethyl-4-phenyl-1-indenyl)(1-indenyl)ZrCl₂,
dimethylsilanediyl(2-methyl-4-(1-naphthyl-1-indenyl)(1-indenyl)ZrCl₂,
diethylgermyl(2-methyl-4-(1-naphthyl)-1-indenyl)(1-indenyl)ZrCl₂, The separation of the stereoisomers is known in principle.

The metallocenes of the formula I can, in principle, be prepared according to the following reaction scheme:

$$H_2R^c + BuytlLi \longrightarrow HR^cLi$$
$$H_2R^d + BuytlLi \longrightarrow HR^dLi$$
$$\xrightarrow{X-(CR^8R^9)_m-R^7(CR^8R^9)_nX}$$

$$HR^c-(CR^8R^9)_m-R^7-(CR^8R^9)_n-R^dH \xrightarrow{2 \text{ BuytlLi}}$$

$$LiR^c-(CR^8R^9)_m-R^7-(CR^8R^9)_n-R^dLi \xrightarrow{M^2Cl_4}$$

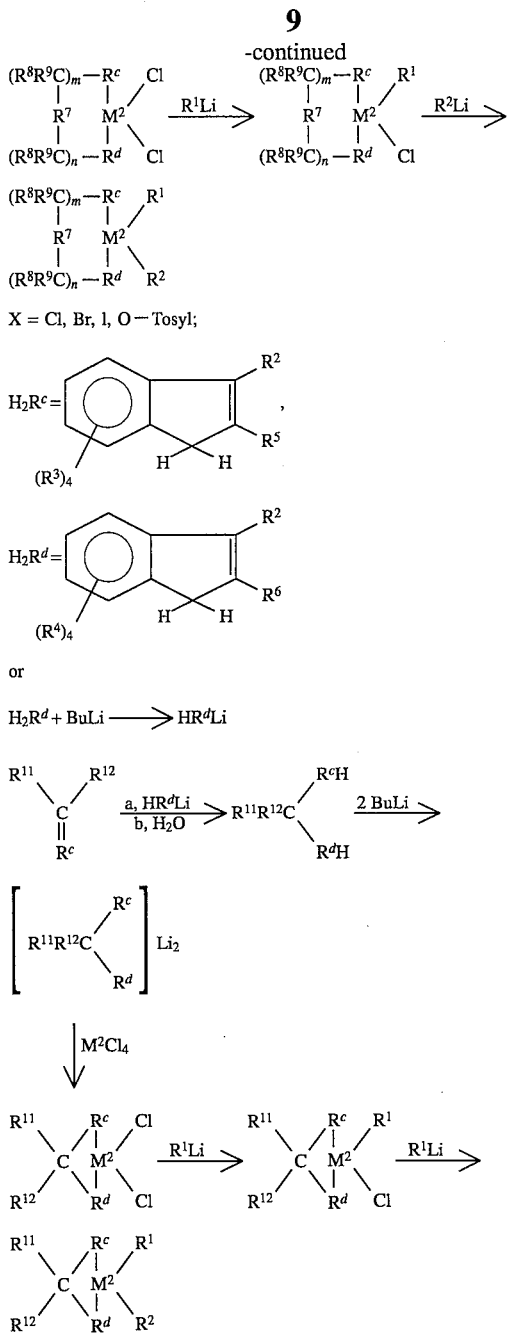

X = Cl, Br, I, O—Tosyl;

(cf. Journal of Organomet. Chem. (1985) pages 63–67 and EP-A 320,762).

The present invention also provides a process for preparing an olefin polymer by polymerization of at least one olefin in the presence of a catalyst containing at least one metallocene as transition metal compound and at least one cocatalyst, wherein the metallocene is a compound of the formula I.

The polymerization can be a homopolymerization or a copolymerization. Preference is given to homopolymerizing or copolymerizing olefins of the formula $R^a$—CH=CH—$R^b$, where $R^a$ and $R^b$ are identical or different and are a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins such as ethylene, propylene, 1-butene, 1-pentene, 1-hexene, 4-methyl-1-pentene or 1-octene, styrene, dienes such as 1,3-butadiene or 1,4-hexadiene and cyclic olefins such as norbornene, tetracyclododecene, norbornadiene or vinylnorbornene.

In the process of the invention, preference is given to homopolymerizing ethylene or propylene, or copolymerizing ethylene with one or more 1-olefins having 3–20 carbon atoms, such as propylene, and/or one or more dienes having 4–20 carbon atoms, such as 1,3-butadiene. Examples of copolymers are ethylene/propylene copolymers, ethylene/propylene/1,4-hexadiene copolymers, ethylene/propylene/5-ethylidene-2-norbornene copolymers or ethylene/norbornene copolymers.

The process of the invention is particularly suitable for preparing isotactic olefin polymers.

The polymerization is preferably carried out at a temperature of from 0° to 200° C., particularly preferably from 50° to 80° C. The pressure is preferably from 0.5 to 100 bar, in particular from 5 to 64 bar.

The polymerization can be carried out in solution, in suspension or in the gas phase, continuously or batchwise, in one or more stages.

Preferably, the catalyst used in the process of the invention Contains one metallocene and one cocatalyst. It is also possible to use mixtures of two or more metallocenes, in particular for preparing polyolefins having a broad or multimodal molecular weight distribution.

In principle, the cocatalyst used in the process of the invention can be any compound which, owing to its Lewis acidity, can convert the neutral metallocene into a cation and stabilize the latter ("lablie coordination"). In addition, the cocatalyst or the anion formed therefrom should undergo no further reactions with the metallocene cation formed (EP 427 697). Cocatalysts used are preferably aluminum and/or boron compounds.

As aluminum compound, preference is given in the process of the invention to using an aluminoxane, in particular of the formula II

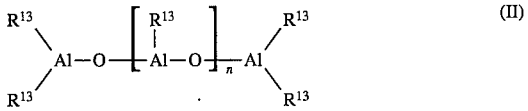

for the linear type and/or of the formula III

for the cyclic type, where in the formulae II and III the radicals $R^{13}$ can be identical or different and are a $C_1$–$C_6$-alkyl group, a $C_1$–$C_6$-fluoroalkyl group, a $C_6$–$C_8$-aryl group, a $C_1$–$C_6$-fluoroaryl group or hydrogen and n is an integer from 0 to 50, or, in place of the aluminoxane, a mixture of an aluminoxane with a compound $AlR^{14}_3$, where $R^{14}$ is as defined for $R^{13}$, is used.

Preferably, the radicals $R^{13}$ are identical and are methyl, isobutyl, phenyl or benzyl, particularly preferably methyl.

If the radicals $R^{13}$ are different, then they are preferably methyl and hydrogen or alternatively methyl and isobutyl, where hydrogen or isobutyl are preferably present in an amount of from 0.01 to 40% (of the radicals $R^{13}$). Instead of the aluminoxane, the cocatalyst used in the polymerization can be a mixture consisting of aluminoxane and $AlR^{14}_3$, where $R^{14}$ is as defined for $R^{13}$. $R^{14}$ is preferably methyl, ethyl, isobutyl, phenyl or benzyl.

The aluminoxane can be prepared in various ways by known methods. One of the methods is, for example, to react an aluminum hydrocarbon compound and/or a hydridoaluminum hydrocarbon compound with water (gaseous, solid, liquid or bound, for example as water of crystallization) in an inert solvent (such as, for example, toluene). To prepare an aluminoxane having different alkyl groups $R^{13}$, two different aluminum trialkyls ($AlR^{13}_3+AlR'^{13}_3$) corresponding to the desired composition are reacted with water (cf. S, Pasynkiewicz, Polyhedron 9 (1990) 429 and EP-A 302 424).

The exact three-dimensional structure of the aluminoxanes is not known (A. R. Barron et al., *J. Am. Chem. Soc.* 115 (1993) 4971). For example, it is also conceivable that chains or rings join to form larger two-dimensional or three-dimensional structures.

Independently of the method of preparation, all aluminoxane solutions have in common a variable content of unreacted aluminum starting compound which is present in free form or as adduct.

It is possible to preactivate the metallocenes with a cocatalyst, in particular aluminoxane, prior to use in the polymerization reaction. This significantly increases the polymerization activity and improves the particle morphology.

The preactivation of the metallocenes is carried out in solution. Here, the solid metallocenes are preferably dissolved in a solution of the aluminoxane in an inert hydrocarbon. Suitable inert hydrocarbons are aliphatic or aromatic hydrocarbons. Preference is given to using toluene or a $C_6$–$C_{10}$-hydrocarbon.

The concentration of the aluminoxane in the solution is preferably in the range from about 1% by weight to the saturation limit, preferably from 5 to 30% by weight, in each case based on the total solution. The metallocenes can be used in the same concentration, but they are preferably used in an amount of from $10^{-4}$ to 1 mol per mole of aluminoxane. The preactivation time is from 1 minute to 60 hours, preferably from 2 to 60 minutes. It is carried out at a temperature of from $-78°$ to $100°$ C., preferably from $0°$ to $70°$ C.

The metallocene can, if desired together with a cocatalyst, be applied to a support and/or be prepolymerized. For the prepolymerization, use is preferably made of the (or one of the) olefin(s) used in the polymerization.

Suitable supports are, for example, silica gels, aluminum oxides, solid aluminoxane, combinations of aluminoxane on a support such as, for example, silica gel, or other inorganic support materials. Another suitable support material is a polyolefin powder in finely divided form.

A further possible embodiment of the process of the invention comprises using, in place of or in addition to an aluminoxane, a salt-like boron compound of the formula $R_xNH_{4-x}BR'_4$ or the formula $R_3PHBR'_4$ as cocatalyst. Here, x=1,2 or 3, R=alkyl or aryl, identical or different, and R'=aryl which can also be fluorinated or partially fluorinated. In this case, the catalyst consists of the reaction product of the metallocenes with one of the specified compounds (cf. EP-A 277 004).

To remove catalyst poisons present in the olefin, a purification using an aluminum alkyl, for example $AlMe_3$ or $AlEt_3$, is advantageous. This purification can be carried out either in the polymerization system itself, or the olefin is, prior to addition to the polymerization system, brought into contact with the Al compound and subsequently separated off again.

If required, hydrogen is added as molecular weight regulator. The addition of the hydrogen effects an additional strong increase in the polymerization activity.

The total pressure in the polymerization system is from 0.5 to 100 bar. Preference is given to carrying out the polymerization in the industrially particularly important pressure range from 5 to 64 bar.

The metallocenes are preferably used in a concentration, based on the transition metal, of from $10^{-3}$ to $10^{-8}$ mol, preferably from $10^{-4}$ to $10^{-7}$ mol metal per $dm^3$ of solvent or per $dm^3$ of reactor volume. The cocatalyst, such as aluminoxane or an aluminoxane/$AlR^{14}_3$ mixture, is preferably used in a concentration of from $10^{-5}$ to $10^{-1}$ mol, preferably from $10^{-4}$ to $10^{-2}$ mol, per $dm^3$ of solvent or per $dm^3$ of reactor volume, However, higher concentrations are also possible in principle.

If the polymerization is carried out as a suspension or solution polymerization, an inert solvent customary for the Ziegler low-pressure process is used. For example, it is carried out in an aliphatic or cycloaliphatic hydrocarbon, examples which may be mentioned being propane, butane, pentane, hexane, heptane, decane, isooctane, cyclohexane, methylcyclohexane.

Furthermore, a gasoline or hydrogenated diesel oil fraction can be used. It is also possible to use toluene. Preferably, the polymerization is carried out in the liquid monomer.

If inert solvents are used, the monomers are metered in in gaseous or liquid form.

The duration of the polymerization is as desired, since the catalyst system to be used according to the invention shows only a small time-dependent decrease in the polymerization activity.

The isotactic polyolefins prepared by the process of the invention are particularly important for the production of shaped bodies such as films, plates or large hollow bodies (e.g. pipes).

The metallocene of the invention gives, in the industrially important temperature range between $50°$ and $100°$ C. and at a very high polymerization activity, polymers having a high molecular weight and a high melting point.

In addition, no meso form is produced in the synthesis of the metallocene, so that its complicated separation becomes superfluous. Combination of different ligands makes it possible to provide metallocene compounds for preparing polyolefins having tailored properties.

In particular in supported form, the metallocenes of the invention lead to polyolefins having very good particle morphology.

The following examples are intended to illustrate the invention.

Definitions:

VN=viscosity number in $cm^3/g$ $M_w$=weight average molecular weight in g/mol (determined by GPC)

$M_w/M_n$=polydispersity (determined by GPC)

II=isotactic index (mm+½ mr) (determined by $^{13}$C-NMR)

$n_{iso}$=isotactic block length (determined by $^{13}$C-NMR)

$n_{syndio}$=syndiotactic block length (determined by $^{13}$C-NMR)

MFI (230/2.16)=melt flow index determined in accordance with DIN 53735 in dg/min MFI (230/5)=melt flow index determined in accordance with DIN 53735 in dg/min m.p.=melting point determined by DSC in °C. ($20°$ C./min heating and cooling rate)

pr="pseudo-rac": in the case of pseudo-rac compounds, the indenyl ligand skeletons are present in a meso arrangement, but because of the different substitution of the indenyl ligands, a center of chirality is present at the central atom $M^2$, so that the compounds are racemic.

All glass apparatus were dried by heating in vacuo and flushed with argon. All operations were carried out with exclusion of moisture and oxygen in Schlenk vessels. The solvents used were, with the exception of dichloromethane,

EXAMPLE A

Dimethylsilanediyl(2-methyl-1-indenyl)(2-methyl-4-phenyl-1-indenyl)zirconium dichloride (1)

29 ml of a 2.5M solution of butyllithium in hexane were added dropwise at room temperature to a solution of 15 g (73 mmol) of 2-methyl-7-phenylindene (the preparation is described in DE 4 221 244) in 150 ml of toluene and 7.5 ml of Et$_2$O over a period of 30 minutes and the mixture was subsequently stirred for a further 2 hours at 40° C. The suspension was subsequently added dropwise at room temperature to a solution of 35.3 ml (290 mmol) of dimethyldichlorosilane in 100 ml of toluene and the mixture was stirred for a further 3 hours at room temperature. The solvent was removed in vacuo and the residue was dried in vacuo (0.1 torr) and subsequently taken up in 200 ml of toluene. To this solution there was added dropwise at room temperature a suspension of 2-methylindenyllithium (prepared by reaction of 9.5 g (73 mmol) of 2-methylindene in 60 ml of toluene and 6 ml of THF at room temperature with 29 ml of a 2.5M solution of butyllithium in hexane and stirring for a further 1 hour at 40° C.) over a period of 50 minutes and the mixture was subsequently stirred for a further 2 hours at room temperature. The reaction mixture was admixed with 100 ml of water, the phases were separated and the organic phase was washed with 50 ml of water. The solvents were removed in vacuo and the residue was purified by chromatography on 400 g of silica gel (hexane/methylene chloride 9:1). Besides 0.7 g of starting material, 16.1 g (67%) of the ligand system of compound 1 were obtained as a colorless oil.

15.2 ml (40.8 mmol) of a 20% strength solution of butyllithium in toluene were added dropwise at 50° C. to a solution of 8.0 g (20.4 mmol) of the ligand system of compound 1 in 50 ml of toluene over a period of 20 minutes and the mixture was subsequently stirred for a further 2 hours at 100° C. After gas evolution had ceased, the mixture was cooled to −40° C. and admixed with 4.75 g (20.4 mmol) of ZrCl$_4$ and stirred for a further 1 hour at room temperature. It was again cooled to −40° C., admixed with 2 ml of THF and filtered through a G3 Schlenk frit. The filtrate was evaporated to half its volume and left to crystallize at −30° C. The supernatant solution was piperted off from the precipitated solid, the solid was washed three times with 1 ml of toluene each time and 5 ml of hexane each time and subsequently dried. This gave 3.4 g (30%) of the racemic form of compound (1) as a yellow solid.

$^1$H-NMR (100 MHz, CDCl$_2$): 6.9 to 7.8 (m, 14 H, arom. H and β-H), 2.1 (2 s, 6 H, CH$_3$), 1.2 (2 s, 6 H, CH$_3$Si). Mass spectrum: 550 M$^+$, correct disintegration pattern.

After concentration of the filtrate and crystallization at −30° C., a further 2.8 g (25%) of the pseudo-rac form of compound (1) were obtained as a yellow solid.

$^1$H-NMR (100 MHz, CDCl$_3$): 6.7 to 7.7 (m, 14 H, arom. H and β-H-IndH), 2.4 (d, 6 H, CH$_3$); 1.4 and 1.2 (2 s, 6 H, CH$_3$Si).

EXAMPLE B

Dimethylsilanediyl(1-indenyl)(2-methyl-4-phenyl-1-indenyl)zirconium dichloride (2)

A suspension of indenyllithium (prepared by reaction of 10.1 g (87 mmol) of indene (90% pure) in 100 ml of toluene and 5 ml of THF at room temperature with 35 ml of a 2.5M solution of butyllithium in hexane and stirring for a further 1 hour at 40° C.) was added dropwise at room temperature to a solution of 26.1 g (87 mmol) of dimethyl(2-methyl-4-phenylindene)chlorosilane in 200 ml of toluene and 10 ml of THF over a period of 50 minutes and the mixture was subsequently stirred for a further 2 hours at room temperature. The reaction mixture was admixed with 100 ml of H$_2$O, the phases were separated and the organic phase was washed with 50 ml of H$_2$O. The solvents were removed in vacuo and the residue was purified by crystallization (hexane/dichloromethane). This gave 18.8 g (56%) of the ligand system of compound 2 as a colorless solid, 19.7 ml (52.8 mmol) of a 20% strength solution of butyllithium in toluene were added dropwise at 50° C. to a solution of 10.0 g (26.4 mmol) of the ligand system of compound 2 in 80 ml of toluene under argon over a period of 20 minutes and the mixture was subsequently stirred for a further 2 hours at 100° C. After gas evolution had ceased, the mixture was cooled to −40° C. and admixed with 6.15 g (25.4 mmol) of ZrCl$_4$ and stirred for a further 1 hour at room temperature. It was again cooled to −40° C., admixed with 2 ml of THF and filtered through a G3 Schlenk frit. From the filtrate, 3.9 g (26%) of the racemic form of compound (2) crystallized at −20° C. as a yellow solid.

$^1$H-NMR (300 MHz, CDCl$_3$): 6.9 to 7.7 (m, 14 H, arom. H and β-H), 6.2 (d, 1 H, α-IndH), 2.3 (s, 3 H, CH$_3$), 1.3 (2 s, 6 H, CH$_3$Si). Mass spectrum: 538 M$^+$, correct disintegration pattern.

After concentration of the filtrate and crystallization at −30° C., a further 2.3 g (15%) of the pseudo-rac form of compound (2) were obtained as a yellow solid.

$^1$H-NMR (300 MHz, CDCl$_3$): 6.9 to 7.7 (m, 14 H, arom. H and β-H-IndH), 2.35 (s, 3 H, CH$_3$); 1.5 and 1.1 (2 s, 6 H, CH$_3$Si).

EXAMPLE C

Dimethylsilanediyl(2-methyl-4,5-benzo-1-indenyl)(2-methyl-1-indenyl)zirconium dichloride (3)

111 ml of a 2.5M solution of butyllithium in hexane were added dropwise at room temperature to a solution of 50.1 g (278 mmol) of 2-methyl-4,5-benzoindenyl (the preparation is described in EP 549 900) in 500 ml of toluene and 25 ml of Et$_2$O over a period of 30 minutes and the mixture was subsequently stirred for a further 2 hours at 40° C. The suspension was subsequently added dropwise at room temperature to a solution of 135 ml (1112 mmol) of dimethyldichlorosilane in 200 ml of toluene and the mixture was stirred for a further 3 hours at room temperature. The solvent was removed in vacuo, the residue was dried in vacuo (0.1 torr) and subsequently taken up in 200 ml of toluene. The suspension is filtered off from the lithium chloride and the solvent of the filtrate is removed in vacuo. This gives 43 g (57%) of a red oily product.

14.9 g (51.9 mmol) of dimethyl(2-methyl-4,5-benzoindenyl)chlorosilane were initially charged in 60 ml of THF and a suspension of 2-methylindenyllithium (prepared by reaction of 7.1 g (54.5 mmol) of 2-methylindene in 20 ml of THF with 21.8 ml of a 2.5M solution of butyllithium in hexane and stirring for a further 1 hour at 40° C.) was added dropwise at room temperature over a period of 15 minutes and the mixture was subsequently stirred for a further 2 hours at room temperature. The reaction mixture was admixed with 100 ml of water, the phases were separated and the organic phase was washed with 50 ml of water. The solvents were removed in vacuo and the residue was purified by chromatography on 400 g of silica gel (hexane/methylene chloride 9:1). This gave 8.18 g (43%) of the ligand system of compound 3 as a colorless oil.

9.6 ml (24 mmol) of a 20% strength solution of butyllithium in toluene were added dropwise at room temperature to a solution of 4.18 g (11.4 mmol) of the ligand system of compound 3 in 50 ml of toluene/5 ml of THF over a period of 20 minutes and the mixture was subsequently stirred for a further 2 hours at 50° C. After gas evolution had ceased, the mixture was cooled to −40° C., admixed with 2.33 g (10 mmol) of $ZrCl_4$ and stirred for a further 1 hour at room temperature. The suspension was filtered through a G3 frit, washed twice with 20 ml of toluene and the residue on the frit was dried in vacuo. This gives 3.36 g (56%) of a product mixture comprising rac and "pseudo-rac" compound in a ratio of 3:2. The product mixture was extracted with 100 ml of $CH_2Cl_2$, the filtrate was evaporated to ⅕ of its volume and stored at −30° C. until crystallization occurred. This gave 1.1 g of the "pseudo-rac" complex as a yellow solid.

$^1$H-NMR (100 MHz, $CDCl_3$): δ=7.75 to 7.00 (m, 11 H, arom. H and benzoindenyl-H), 6.70 (m, 1 H, Ind-H), 2.52/ 2.48 (each s, each 3 H, $CH_3$-Ind and $CH_3$-benzo); 1.40/1.25 (each s, each 3 H, $(CH_3)_2$)Si.

Further extraction of the residue on the frit with 200 ml of $CH_2Cl_2$, evaporation of the filtrate to 20 ml, cooling to −30° C., and filtering off the solid formed on a frit gave 1.4 g of the rac compound.

$^1$H-NMR (100 MHz, $CDCl_3$): δ=8.03 to 7.10 (m, 11 H, arom. H and benzoindenyl-H), 6.78 (m, 1 H, Ind-H), 2.29/ 2.26 (each s, each 3 H, $CH_3$-Ind and $CH_3$-benzo); 1.30 (s, 6 H, $(CH_3)_2$Si).

EXAMPLE D rac-Diethylgermaniumdiyl(2-methyl-4-phenylindenyl)(2-ethylindenyl)zirconium dichloride (4)

Using a method similar to that of Example A, 20 g (97 mmol) of 2-methyl-4-phenylindene, 97 mmol of butyllithium, 60.5 g (300 mmol) of diethyldichlorogermanium, 13.9 g (97 mmol) of 2-ethylindene, 97 mmol of butyllithium and chromatography on silica gel gave 30.2 g (65%) of the ligand system diethylgermaniumdiyl(2-methyl-4-phenylindenyl)(2-ethylindenyl).

10 g (20.8 mmol) of the ligand system give, after deprotonation with 42 mmol of butyllithium and reaction with 4.7 g (20 mmol) of zirconium tetrachloride, after filtration and crystallization, 3.6 g (28%) of rac-diethylgermaniumdiyl(2-methyl-4-phenylindenyl)(2-ethylindenyl)zirconium dichloride.

EXAMPLE E rac-Dimethylsilanediyl(2,4,6-trimethylindenyl)(2-methyl-4-phenylindenyl)zirconium dichloride (5)

Using a method similar to that of Example A, 10 g (63 mmol) of 2,4,6-trimethylindene, 63 mmol of butyllithium, 32.3 g (250 mmol) of dimethyldichlorosilane, 13.0 g (63 mmol) of 2-methyl-4-phenylindene, 63 mmol of butyllithium and chromatography on silica gel gave 18.8 g (71%) of the ligand system dimethylsilanediyl(2,4,6-trimethylindenyl)(2-methyl-4-phenylindenyl).

10 g (23.7 mmol) of the ligand system give, after deprotonation with 47.4 mmol of butyllithium and reaction with 5.5 g (23.7 mmol) of zirconium tetrachloride, after filtration and crystallization, 4.3 g (31%) of rac-dimethylsilanediyl(2, 4,6-trimethylindenyl)(2-methyl-4-phenylindenyl)zirconium dichloride.

EXAMPLE F rac-Dimethylsilanediyl(2-methyl-4,6-diisopropylindenyl)(2-methylindenyl)zirconium dichloride (6)

Using a method similar to that of Example A, 10 g (47 mmol) of 2-methyl-4,6-diisopropylindene, 47 mmol of butyllithium, 24.3 g (188 mmol) of dimethyldichlorosilane, 6.1 g (47 mmol) of 2-methylindene, 47 mmol of butyllithium and chromatography on silica gel gave 12.2 g (65%) of the ligand system dimethylsilanediyl(2-methyl-4,6-diisopropylindenyl)(2-methylindenyl).

10 g (25 mmol) of the ligand system give, after deprotonation with 50 mmol of butyllithium and reaction with 5.8 g (25 mmol) of zirconium tetrachloride, filtration and crystallization, 3.5 g (25%) cf rac-dimethylsilanediyl(2-methyl-4,6-diisopropylindenyl)(2-methylindenyl)zirconium dichloride.

EXAMPLE G rac-Dimethylgermaniumdiyl(2-methyl-4-phenylindenyl)(2-methylindenyl)zirconium dichloride (7)

Using a method similar to that of Example A, 5 g (24 mmol) of 2-methyl-4-phenylindene, 24 mmol of butyllithium, 16.7 g (96 mmol) of dimethyldichlorogermanium, 3.1 g (24 mmol) of 2-methylindene, 24 mmol of butyllithium and chromatography on silica gel gave 6.1 g (58%) of the ligand system dimethylgermaniumdiyl(2-methyl-4-phenylindenyl)(2-methylindenyl).

5.0 g (11.4 mmol) of the ligand system give, after deprotonation with 22.8 mmol of butyllithium and reaction with 2.7 g (11.4 mmol) of zirconium tetrachloride, filtration and crystallization, 2.2 g (33%) of rac-dimethylgermaniumdiyl (2-methyl-4-phenylindenyl) (2-methylindenyl)zirconium dichloride.

EXAMPLE H rac-Dimethylsilanediyl(2-methylacenaphthindenyl)(2-methyl-4-phenylindenyl)zirconium dichloride (8)

Using a method similar to that of Example A, 10 g (48 mmol) of 2-methylacenaphthindene, 48 mmol of butyllithium, 24.5 g (190 mmol) of dimethyldichlorosilane, 10 g (48 mmol) of 2-methyl-4-phenylindene, 48 mmol of butyllithium and chromatography on silica gel gave 16 g (71%) of the ligand system dimethylsilanediyl (2-methylacenaphthindenyl)(2-methyl-4-phenylindenyl).

10 g (21.3 mmol) of the ligand system give, after deprotonation with 42.6 mmol of butyllithium and reaction with 4.9 g (21.3 mmol) of zirconium 30 tetrachloride, filtration and crystallization, 3.9 g (29%) of rac-dimethylsilanediyl(2-methylacenaphthindenyl)(2-methyl-4-phenylindenyl)zirconium dichloride.

EXAMPLE I rac-Diethylgermaniumdiyl(2-methyl-4-[1-naphthyl]indenyl)(indenyl)zirconium dichloride (9)

Using a method similar to that of Example A, 5 g (19.5 mmol) of 2-methyl-4-[1-naphthyl]indene, 20 mmol of butyllithium, 15.7 g (78 mmol) of diethyldichlorogermanium, 2.5 g (19.5 mmol) of indene: 20 mmol of butyllithium and chromatography on silica gel gave 6.2 g (62%) of the ligand system diethylgermaniumdiyl (2-methyl-4-[1-naphthyl]indenyl)(indenyl).

5.0 g (9.7 mmol) of the ligand system give, after deprotonation with 19.5 mmol of butyllithium and reaction with 2.3 g (9.7 mmol) of zirconium tetrachloride, filtration and crystallization, 1.6 g (24%) of rac-diethylgermaniumdiyl(2-methyl-4-[1-naphthyl]indenyl)(indenyl)zirconium dichloride.

POLYMERIZATIONS

EXAMPLE 1

A dry 24 dm$^3$ reactor was flushed with propylene and charged with 12 dm$^3$ of liquid propylene and 25 cm$^3$ of methylaluminoxane solution in toluene (corresponding to 37 mmol of Al, average degree of oligomerization was n=20). The contents were stirred at 30° C. for 5 minutes at 250 rpm. In parallel thereto, 0.9 mg of rac-dimethylsilanediyl (2-methyl-4-phenyl-1-indenyl)(2-methyl-1-indenyl)zirconium dichloride was dissolved in 10 cm$^3$ of methylaluminoxane solution in toluene (17 mmol of Al) and preactivated by being left to stand for 5 minutes. The solution was added to the reactor and polymerization was carried out for 1 hour at 70° C. This gave 0.73 kg of polypropylene. The metallocene activity was 811 kg PP/g metallocene×h. The following properties were determined on the polymer:

VN=379 cm$^3$/g; $M_w$=537,500 g/mol, $M_w/M_n$2.2; MFI (230/2)=0.3 dg/min, MFI (230/5)=1.5 dg/min; m.p. 155° C., II =98.3%, $n_{iso}$=86.

COMPARATIVE EXAMPLE 1

The procedure of Example 1 was repeated, but using the metallocene rac-dimethylsilanediylbis(2-methyl-1-indenyl)zirconium dichloride. The metallocene activity was 350 kg PP/g metallocene×h.

VN=180 cm$^3$/g; $M_w$=187,000 g/mol, $M_w/M_n$=2.5; MFI (230/2)=13 dg/min, MFI (230/5)=37 dg/min; m.p. 145° C.

EXAMPLE 2

The procedure of Example 1 was repeated, but using 2.5 mg of the metallocene and a polymerization temperature of 50° C. The metallocene activity was 398 kg PP/g metallocene×h and the following data were determined on the polymer:

VN=553 cm$^3$/g; $M_w$=811,000 g/mol, $M_w/M_n$=2.3; MFI (230/2)=0.1 dg/min, MFI (230/5)=0.5 dg/min; m.p. 158° C.

COMPARATIVE EXAMPLE 2

Example 2 was repeated, using the metallocene rac-dimethylsilanediylbis(2-methyl-1-indenyl)zirconium dichloride. The metallocene activity was 125 kg PP/g metallocene×h.

VN=250 cm$^3$/g; $M_w$=318,000 g/mol, $M_w/M_n$=2.1; MFI (230/5)=10 dg/min; m.p. 148° C.

EXAMPLE 3

The procedure of Example 1 was repeated, but additionally using 5 standard dm$^3$ of hydrogen. The metallocene activity was 1187 kg PP/g metallocene×h.

VN=226 cm$^3$/g; $M_w$=282,500 g/mol, $M_w/M_n$=1.9; MFI (230/2)=7 dg/min, MFI (230/5)=20 dg/min; m.p. 160° C., II=98.6, $n_{iso}$=125. The example demonstrates that the molecular weight can be readily regulated using hydrogen.

EXAMPLE 4

The procedure of Example 1 was repeated, but using the metallocene in a rac: "pseudo-rac" mixture of 1:1. The metallocene activity was 656 kg PP/g metallocene×h.

VN=351 cm$^3$/g; $M_w$=502,500 g/mol, $M_w/M_n$=2.3; MFI (230/5)=2.6 dg/min; m.p. 155 ° C.

EXAMPLE 5

The procedure of Example 4 was repeated, but using a 1:5 rac to "pseudo-rac" fraction of the metallocene. The metallocene activity was 510 kg PP/g metallocene×h.

VN=315 cm$^3$/g; $M_w$=354,500 g/mol, $M_w/M_n$=2.3; MFI (230/5)=3.0 dg/min; m.p. 153° C.

EXAMPLE 6

Example 5 was repeated at a polymerization temperature of 50° C. The metallocene activity was 215 kg PP/g metallocene×h.

VN=451 cm$^3$/g; $M_w$=587,500 g/mol, $M_w/M_n$=2.6; MFI (230/5)=1.6 dg/min; m.p. 159° C.

COMPARATIVE EXAMPLE 3

Example 5 was repeated using the metallocene meso-dimethylsilanediylbis(2-methyl-1-indenyl)zirconium dichloride. No polymer powder was obtained. The mass obtained was soft and sticky, the amorphous mass had no melting point and the VN was 42 cm$^3$/g. $^{13}$C-NMR measurements show that this is a pure atactic polymer ($n_{iso}$=2, $n_{syndio}$=2, II=52%). A melt flow index value could likewise not be determined because of the fluidity of the polymer. The metallocene activity in the polymerization was 8.6 kg PP/g metallocene×h.

COMPARATIVE EXAMPLE 4

Example 5 was repeated using the metallocene meso-dimethylsilanediylbis(2-methyl-4-phenyl-1-indenyl)zirconium dichloride. The polymer obtained corresponded in its properties to that from Comparative Example 3, and is likewise atactic polypropylene. The VN was 110 cm$^3$/g, the metallocene activity was 52 kg PP/g metallocene×h.

EXAMPLE 7

The procedure of Example 1 was repeated, but using the metallocene rac-dimethylsilanediyl(2-methyl-4,5-benzo-1-indenyl)(2-methyl-1-indenyl)zirconium dichloride. The metallocene activity was 496 kg PP/g metallocene×h.

VN=164 cm$^3$/g; $M_w$=190,000 g/mol, $M_w/M_n$=2.2; MFI (230/2)=8 dg/min, MFI (230/5)=25 dg/min; m.p. 144° C.

EXAMPLE 8

The procedure of Example 2 was repeated, but using the metallocene from Example 7. The metallocene activity was 245 kg PP/g metallocene×h.

VN=274 cm$^3$/g; $M_w$=349,500 g/mol, $M_w/M_n$=2.3; MFI (230/2)=2 dg/min, MFI (230/5)=6 dg/min; m.p. 148° C., II=97.5%, $n_{iso}$=66.

EXAMPLE 9

The procedure of Example 2 was repeated, but using the metallocene dimethylsilanediyl(2-methyl-4,5-benzo-1-indenyl)(2-methyl-1-indenyl)zirconium dichloride in a rac:

"pseudo-rac" 1:10 mixture. The metallocene activity was 214 kg PP/g metallocene×h.

VN=269 cm$^3$/g; M$_w$=382,000 g/mol, M$_w$/M$_n$=2.2; MFI (230/2)=3.1 dg/min, MFI (230/5)=9 dg/min; m.p. 146° C.

EXAMPLE 10

The procedure of Example 2 was repeated, but using the metallocene dimethylsilanediyl(2-methyl-4,5-benzo-1-indenyl)(2-methyl-1-indenyl)zirconium dichloride in a rac:pr ratio of 3:2, as is present in the filtrate from the synthesis after filtration through a G3 frit. The metallocene activity was 249 kg PP/g metallocene×h.

VN=282 cm$^3$/g; M$_w$=384,500 g/mol, M$_w$/M$_n$=2.2; MFI (230/2)=2 dg/min, MFI (230/5)=5.5 dg/min; m.p. 148° C., II =97.6%, n$_{iso}$=59.

EXAMPLE 11

The procedure of Example 1 was repeated, but using the metallocene rac-dimethylsilanediyl(2-methyl-4-phenyl-1-indenyl)(1-indenyl)zirconium dichloride. The metallocene activity was 935 kg PP/g metallocene×h.

VN=136 cm$^3$/g; M$_w$=128,500 g/mol, M$_w$/M$_n$=2.0; MFI (230/2)=35 dg/min; m.p. 151° C.

EXAMPLE 12

The procedure of Example 2 was repeated, but using the metallocene of Example 11. The metallocene activity was 399 kg PP/g metallocene×h. VN=190 cm$^3$/g; M$_w$=204,500 g/mol, M$_w$/M$_n$=2.0; MFI (230/2)=9 dg/min; m.p. 154° C.

EXAMPLE 13

The procedure of Example 2 was repeated, but using the metallocene dimethylsilanediyl(2-methyl-4,5-benzo-1-indenyl)(2-methyl-1-indenyl)zirconium dichloride in a rac: "pseudo-rac" 1:8 mixture. The metallocene activity was 228 kg PP/g metallocene×h. VN=182 cm$^3$/g; M$_w$=201,500 g/mol, M$_w$/M$_n$=2.2; MFI (230/2)=12.5 dg/min; m.p. 154° C.

EXAMPLE 14

The procedure of Example 11 was repeated, but using the metallocene dimethylsilanediyl(2-methyl-4-phenyl-1-indenyl)(1-indenyl)zirconium dichloride in the isomer mixture obtained from the synthesis of rac:pr=1:0.6. The metallocene activity was 382 kg PP/g metallocene×h.

VN=184 cm$^3$/g; M$_w$=216,000 g/mol, M$_w$/M$_n$=3.3; MFI (230/2)=8 dg/min; m.p. 155° C., II=98.0%, n$_{iso}$=82.

COMPARATIVE EXAMPLE 5

The procedure of Example 11 was repeated, but using the metallocene rac-dimethylsilanediylbis(1-indenyl)zirconium dichloride which is not according to the invention. The metallocene activity was 559 kg PP/g metallocene×h.

VN=43 cm$^3$/g; M$_w$=34,900 g/mol, M$_w$/M$_n$=2.5; MFI no longer measurable, since the polymer too fluid; m.p. 137° C.

EXAMPLE 15

Example 1 was repeated, but using the metallocene dimethylsilanediyl(2-ethyl-4-phenyl-1-indenyl)(2-methyl-1-indenyl)zirconium dichloride, the ratio rac:pr was 4:1.5 (from the synthesis). The metallocene activity was 671 kg PP/g metallocene×h.

VN=357 cm$^3$/g; M$_w$=494,000 g/mol, M$_w$/M$_n$=2.4; MFI (230/5)=3 dg/min; m.p. 159° C.

EXAMPLE 16

Example 15 was repeated at a polymerization temperature of 50° C. The metallocene activity was 329 kg PP/g metallocene×h.

VN=524 cm$^3$/g; M$_w$=698,000 g/mol, M$_w$/M$_n$=2.0; MFI (230/5)=1 dg/min; m.p. 163° C.

EXAMPLE 17

Example 1 was repeated, but using the metallocene dimethylsilanediyl(2-methyl-4-(1-naphthyl)-1-indenyl)(2-methyl-1-indenyl)zirconium dichloride, the rac:pr ratio was 3:1.4 (from the synthesis).

The metallocene activity was 749 kg PP/g metallocene×h.

VN=449 cm$^3$/g; M$_w$=647,500 g/mol, M$_w$/M$_n$=2.2; m.p. 156° C.

EXAMPLE 18

Example 1 was repeated, but using the metallocene 1,2-ethanediyl(2-ethyl-4-(1-naphthyl)-1-indenyl)(2-methyl-1-indenyl)zirconium dichloride, the rac:pr ratio was 2.5:1 (from the synthesis).

The metallocene activity was 519 kg PP/g metallocene×h.

VN=401 cm$^3$/g; M$_w$=584,500 g/mol, M$_w$/M$_n$=2.0; m.p. 152° C.

EXAMPLE 19

Example 1 was repeated, but adding 2.5 standard dm$^3$ of hydrogen to the reactor prior to addition of the propylene and additionally metering in 60 g of ethylene as comonomer during the polymerization. The metallocene activity was 1386 kg copolymer/g metallocene×h. The following properties were determined on the polymer: ethylene content= 4.1% by weight, VN=179 cm$^3$/g; M$_w$=217,500 g/mol, M$_w$/M$_n$=2.0; m.p.= 136° C., 0.75% of the polymer can be extracted with boiling hexane.

EXAMPLE 20

Example 19 was repeated using 60 g of 1-hexene as comonomer. The metallocene activity was 998 kg copolymer/g metallocene×h. The following properties were determined on the polymer: hexene content=5.6% by weight, VN=208 cm$^3$/g; M$_w$=237,000 g/mol, M$_w$/M$_n$=1.9; m.p.= 127° C.

EXAMPLE 21

Example 19 was repeated using 1-butene as comonomer. The butene content in the polymer was 5.1% by weight, the melting point was 130° C.

EXAMPLE 22

A dry 150 dm$^3$ reactor was flushed with nitrogen and charged at 20° C. with 100 dm$^3$ of a de-aromatized petroleum fraction having a boiling range from 100° to 120° C. The gas space was then flushed free of nitrogen by pressurizing with 2 bar of propylene and depressurizing 5 times. After addition of 50 l of liquid propylene 64 cm$^3$ of methylaluminoxane solution in toluene (corresponding to 100 mmol of Al) were added and the reactor contents were heated to 50° C. A hydrogen content in the reactor gas space of 1.5% was set by metering in hydrogen and subsequently kept constant during the entire propylene polymerization time by metering in further amounts gas chromatography, on-line measurement). 15 mg of the metallocene rac-diethylgermyl (2-methyl-4-phenyl-1-indenyl)(2-ethyl-1-indenyl)zirconium dichloride were dissolved in 16 cm$^3$ of methylaluminoxane solution in toluene (corresponding to 25 mmol of Al) and after 15 minutes were added to the reactor. By means of cooling, the reactor was kept at a polymerization temperature of 55° C. for 5 hours. After venting hydrogen and propylene to a propylene pressure of 1.5 bar in the reactor and addition of 2.5 kg of ethylene, polymerization was continued for a further 3 hours at 50° C.

The reactor contents were discharged onto a pressure filter, the product was separated off from the residual suspension medium by means of steam distillation and was dried for 24 hours at 80° C./200 mbar. This gave 21.5 kg of block copolymer powder, corresponding to a metallocene activity of 179.2 kg copolymer/g metallocene×h. The block copolymer contained 10.8% by weight of ethylene, fractionation gave a content of 22.7% by weight of ethylene/propylene rubber, the glass transition temperature of the rubber was −54.5° C. The MFI (230/2) of the total polymer was 16 dg/min.

EXAMPLE 23

Example 19 was repeated, but, besides 500 g of ethylene, an additional 150 ml of 5-ethylidene-2-norbornene were metered into the reactor during the polymerization time. The polymerization temperature was 50° C. This gave a terpolymer rubber having a glass transition temperature of −59.8° C. The ethylene content in the polymer was 42% by weight and the ethylidenenorbornene content was 4.8% by weight.

EXAMPLE 24

Use of a supported metallocene as catalyst:

a) Preparation of the supported cocatalyst

The supported cocatalyst was prepared as described in EP 92 107 331.8 in the following manner in a stainless steel reactor of explosion-protected design having a pump circulation system of 60 bar pressure rating, with inert gas supply, temperature control by jacket cooling and a second cooling circuit via a heat exchanger on the pump circulation system. The pump circulation system drew in the reactor contents via a connection in the bottom of the reactor by means of a pump and pressed it into a mixer and through a rising line via a heat exchanger back into the reactor. The mixer was connected in such a way that in the inlet there was a constricted tube cross section where there arose an increased flow velocity and into the turbulence zone of which there was introduced axially and counter to the flow direction a narrow feed line through which, in a pulsed manner, each of a defined amount of water at 40 bar of argon pressure could be fed in. The reaction was monitored via a sampler on the pump circuit.

The above-described reactor having a volume of 16 dm$^3$ was charged under inert conditions with 5 dm$^3$ of decane. 0.3 dm$^3$ (=3.1 mol) of trimethylaluminum were added at 25° C. 250 g of silica gel SD 3116-30 (Grace AG), which were previously dried at 120° C. in an argon fluidized bed, were then metered through a solids funnel into the reactor and homogeneously distributed by means of the stirrer and the pump circulation system. A total amount of 45.9 g of water was added to the reactor in portions of 0.1 cm$^3$ over a period of 2 hours, each every 15 seconds. The pressure, caused by argon and the gases evolved, was kept constant at 10 bar by means of pressure regulating valves. After all the water had been introduced, the pump circulation system was switched off and the stirring was continued for a further 5 hours at 25° C. The solvent was removed via a pressure filter and the cocatalyst solid was washed with decane and then dried in vacuo. The solid isolated contained 18.4% by weight of aluminum, 15 g of this solid (102 mmol of Al) were suspended in 100 cm$^3$ of toluene in a stirrable vessel and cooled to −30° C. At the same time, 200 mg of rac/pr 7:1 Me$_2$Si(2,4,6-trimethyl-1-indenyl)(2-methyl-4-phenyl-1-indenyl)ZrCl$_2$ were dissolved in 75 cm$^3$ of toluene and added dropwise to the suspension over a period of 30 minutes. The mixture was slowly warmed to room temperature while stirring, with the suspension becoming a red color. Subsequently, the suspension was stirred for one hour at 50° C. and, after cooling to room temperature, the mixture was filtered and the solid was washed 3 times with 100 cm$^3$ of toluene each time and once with 100 cm$^3$ of hexane. The remaining filter residue, which was moist with hexane, was dried in vacuo. This gave 14.2 g of free-flowing, pale red, supported catalyst. Analysis gave a content of 10.9 mg of zirconocene per gram of catalyst.

b) Polymerization 1.2 g of the catalyst prepared under a) were suspended in 25 cm$^3$ of a de-aromatized petroleum fraction having a boiling range from 100° to 120° C.

Parallel thereto, a dry 24 dm$^3$ reactor was first flushed with nitrogen and subsequently with propylene and charged with 12 dm$^3$ of liquid propylene and with 1.5 dm$^3$ of hydrogen. 3 cm$^3$ of triisobutylaluminum (12 mmol) were then diluted with 30 ml of hexane and added to the reactor, and the mixture was stirred at 30° C. for 15 minutes. Subsequently, the catalyst suspension was added to the reactor, the mixture was heated to the polymerization temperature of 80° C. (10° C./min) and the polymerization system was kept at 80° C. for 1 hour by means of cooling. The polymerization was stopped by addition of 20 ml of isopropanol. The excess monomer was vented, the polymer was dried in vacuo. This gave 2.78 Kg of polypropylene powder. The metallocene activity was thus 212.5 kg PP/g Met.×h. The following properties were determined on the polymer:

VN=298 cm$^3$/g; M$_w$=378,500 g/mol, M$_w$/M$_n$=2.0; MFI (230/5)=3.9 dg/min; MFI (230/2)=1.2 dg/min; m.p. 150° C.

Powder morphology: no fines<200/µm, average particle diameter d$_{50}$=735 µm, no oversize>1500/µm, narrow particle size distribution s=ln(d$_{50}$/d$_{16}$)=0.25; bulk density 495 g/dm$^3$.

EXAMPLES 25 TO 28

Example 1 was repeated, but the metallocenes used were the compounds listed in Table 1. Activities and polymer data are likewise shown in Table 1.

TABLE 1

Ethylene polymerizations (Examples D to H)

| Example | Metallocene | Activity [kg PP/g metallocene × h] | VN [cm³/g] | m.p. (°C.) | $M_w/M_n$ | MFI (230/2) (dg/min) |
|---|---|---|---|---|---|---|
| 25 | rac-Me₂Si(2-methyl-4,6-diisopropyl-1-indenyl)-(2-methyl-1-indenyl)ZrCl₂ | 458 | 149 | 145 | 2,1 | 25 |
| 26 | rac-Me₂Ge(2-methyl-4-phenyl-1-indenyl)-(2-methyl-1-indenyl)ZrCl₂ | 924 | 407 | 155 | 2,4 | 0,5 |
| 27 | rac-Me₂Si(2-methyl-α-acenaphth-1-indenyl)-(2-methyl-4-phenyl-1-indenyl)ZrCl₂ | 1100 | 587 | 157 | 2,3 | 0,1 |
| 28 | rac-Et₂Ge(2-methyl-4-[1-naphthyl]-1-indenyl)-(indenyl)ZrCl₂ | 865 | 186 | 152 | 2,0 | 8,5 |

EXAMPLES 29 TO 34

A dry 1.5 dm³ reactor was flushed with nitrogen and charged at 20° C. with 0.75 dm³ of a de-aromatized petroleum fraction having a boiling range from 100° to 120° C. The gas space of the reactor was then flushed free of nitrogen by pressurizing with 2 bar of ethylene and depressurizing 5 times. 3.75 cm³ of methylaluminoxide solution in toluene (5 mmol of Al, n=18) were then added. Whilst stirring, the reactor was heated to 30° C. (over a period of 15 minutes) and, at a stirring speed of 500 rpm, a total pressure of 5 bar was set by addition of ethylene. In parallel thereto, 0.125 mg of metallocene (for type of compound, see Table 2) was dissolved in 1.25 cm³ of methylaluminoxide solution in toluene (1.67 mmol of Al, n=18) and reacted completely by being left to stand for 15 minutes. The solution was then added to the reactor, the polymerization system was brought to 70° C. and left at this temperature for 1 hour by means of appropriate cooling. During this time, the pressure was maintained at 5 bar by appropriate feeding in of ethylene. The polymerization was then stopped by addition of 2 ml of isopropanol, the polymer was filtered off and dried in vacuo. The results of the polymerizations are shown in Table 2.

EXAMPLES 35 AND 36

Example 24 was repeated at polymerization temperatures of 65° C. (Example 35) and 88° C (Example 36). At the polymerization temperature of 88° C., the polymerization was ended after 30 minutes because of the high polymerization activity. The melting points measured on the polymer were 148° C. (Example 35) and 156° C. (Example 36).

We claim:
1. A process for preparing an olefin polymer comprising the step of polymerizing or copolymerizing at least one olefin in the presence of a catalyst composition comprising at least one metallocene and at least one cocatalyst therefor, wherein the metallocene is a compound of the formula I

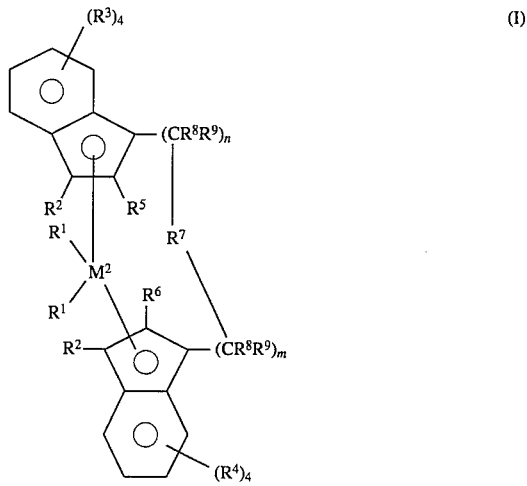

where $M^2$ is a metal of group IVb of the Periodic Table, the radicals $R^1$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{40}$-alkenyl group, a $C_7$–$C_{40}$-arylalkyl group, a $C_7$–$C_{40}$-

TABLE 2

Examples 29 to 34

| Example | Metallocene | Activity [kg PE/g Met. × h] | VN [cm³/g] |
|---|---|---|---|
| 29 | Me₂Si(2-methyl-4-phenyl-1-indenyl)(2-methyl-1-indenyl)ZrCl₂ [rac:pr = 5:1] | 248 | 473 |
| 30 | pr-Me₂Si(2-methyl-4-phenyl-1-indenyl)(2-methyl-1-indenyl)ZrCl₂ | 224 | 482 |
| 31 | Me₂Si(2-methyl-4,5-benzo-1-indenyl)(2-methyl-1-indenyl)ZrCl₂ [rac:pr = 15:1] | 272 | 473 |
| 32 | pr-Me₂Si(2-methyl-4,5-benzo-1-indenyl)(2-methyl-1-indenyl)ZrCl₂ | 296 | 444 |
| 33 | Me₂Si(2-methyl-4-phenyl-1-indenyl)(1-indenyl)ZrCl₂ [rac:pr = 10:1] | 480 | 551 |
| 34 | pr-Me₂Si(2-methyl-4-phenyl-1-indenyl)(1-indenyl)ZrCl₂ | 465 | 461 | alkylaryl group, a $C_8-C_{40}$-arylalkenyl group or a halogen atom, the radicals $R^2$ are identical or different and are hydrogen, a halogen atom, a $C_1-C_{10}$-alkyl group which can be halogenated, a $C_6-C_{10}$-aryl group, a $C_2-C_{10}$-alkenyl group, a $C_7-C_{40}$-arylalkyl group, a $C_7-C_{40}$-alkylaryl group, a $C_8-C_{40}$-arylalkenyl group, a $-NR_2^{10}$, $-OR^{10}$, $-SR^{10}$, $-OSiR_3^{10}$, $-SiR_3^{10}$ or $-PR_2^{10}$ radical, where $R^{10}$ is a halogen atom, a $C_1-C_{10}$-alkyl group or a $C_6-C_{10}$-aryl group, the radicals $R^3$ are identical or different and are a hydrogen atom, a halogen atom, a $C_1-C_{20}$-alkyl group, a $C_1-C_{20}$-fluoroalkyl group, a $C_6-C_{30}$-aryl group, a $C_6-C_{30}$-fluoroaryl group, a $C_7-C_{40}$-alkoxy group, a $C_8-C_{40}$-alkenyl group, a $C_7-C_{40}$-arylalkyl group, a $C_8-C_{40}$-arylalkenyl group, a $C_7-C_{40}$-alkylaryl group, a $-NR_2^{10}$, $-OR^{10}$, $-SR^{10}$, $-OSiR_3^{10}$, $-SiR_3^{10}$ or $-PR_2^{10}$ radical, where $R^{10}$ is a halogen atom, a $C_1-C_{10}$-alkyl group or a $C_6-C_{10}$-aryl group, or two or more radicals $R^3$ together with the atoms connecting them form a ring system; but not all radicals $R^3$ are hydrogen when all radicals $R^4$ are hydrogen;

the radicals $R^4$ are identical or different and are a hydrogen atom, a halogen atom, a $C_1-C_{20}$-alkyl group, a $C_1-C_{20}$-fluoroalkyl group, a $C_6-C_{30}$-aryl group, a $C_6-C_{30}$-fluoroaryl group, a $C_1-C_{20}$-alkoxy group, a $C_2-C_{20}$-alkenyl group, a $C_7-C_{40}$-arylalkyl group, a $C_8-C_{40}$-arylalkenyl group, a $C_7-C_{40}$-arylyalkyl group, a $C_8-C_{40}$-arylalkenyl group, a $C_7-C_{40}$-alkylaryl group, a $-NR_2^{10}$, $-OR^{10}$, $-SR^{10}$, $-OSiR_3^{10}$, $-SiR_3^{10}$ or $-PR_2^{10}$ radical, where $R^{10}$ is a halogen atom, a $C_1-C_{10}$-alkyl group or a $C_6-C_{10}$-aryl group, or two or more radicals $R^4$ together with the atoms connecting them form a ring system; but not all radicals $R^4$ are hydrogen when all radicals $R^3$ are hydrogen;

$R^5$ is a halogen atom, a $C_1-C_{10}$-alkyl group, which can be halogenated, a $C_6-C_{10}$-aryl group, a $C_2-C_{10}$-alkenyl group, a $C_7-C_{40}$-arylalkyl group, a $C_7-C_{40}$-alkylaryl group, a $C_8-C_{40}$-arylalkenyl group, a $-NR_2^{10}$, $-OR^{10}$, $-SR^{10}$, $-OSiR_3^{10}$, $-SiR_3^{10}$ or $-PR_2^{10}$ radical, where $R^{10}$ is a halogen atom, a $C_1-C_{10}$-alkyl group or a $C_6-C_{10}$-aryl group, $R^6$ is a hydrogen atom, a halogen atom, a $C_1-C_{10}$-alkyl group, which can be halogenated, a $C_6-C_{10}$-aryl group, a $C_2-C_{10}$-alkenyl group, a $C_7-C_{40}$-arylalkyl group, a $C_7-C_{40}$-alkyloxy group, a $C_8-C_{40}$-arylalkenyl group, a $-NR_2^{10}$, $-OR^{10}$, $-SR^{10}$, $-OSiR_3^{10}$, $-SiR_3^{10}$ or $-PR_2^{10}$ radical, where $R^{10}$ is a halogen atom, a $C_1-C_{10}$-alkyl group or a $C_6-C_{10}$-aryl group, $R^7$ is

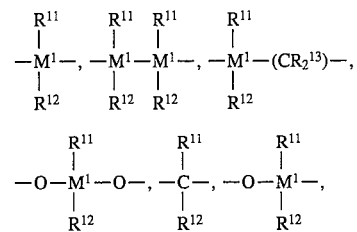

$=BR^{11}$, $=AlR^{11}$, $-Ge-$, $-Sn-$, $-O-$, $-S-$, $=SO$, $=SO_2$, $=NR^{11}$, $=CO$, $=PR^{11}$ or $=P(O)R^{11}$, where $R^{11}$, $R^{12}$ and $R^{13}$ are identical or different and are a hydrogen atom, a halogen atom, a $C_1-C_{20}$-alkyl group, a $C_1-C_{20}$-fluoroalkyl group, a $C_6-C_{30}$-aryl group, a $C_6-C_{30}$-fluoroaryl group, a $C_1-C_{20}$-alkoxy group, a $C_2-C_{20}$-alkenyl group, a $C_7-C_{40}$-arylalkyl group, a $C_8-C_{40}$-arylalkenyl group, a $C_7-C_{40}$-alkylaryl group, or $R^{11}$ and $R^{12}$ or $R^{11}$ and $R^{13}$ together with the atoms connecting them form a ring, $M^1$ is silicon, germanium or tin, $R^8$ and $R^9$ are identical or different and are a hydrogen atom, a halogen atom, a $C_1-C_{20}$-alkyl group, a $C_1-C_{20}$-fluoroalkyl group, a $C_6-C_{30}$-aryl group, a $C_6-C_{30}$-fluoroaryl group, a $C_1-C_{20}$-alkoxy group, a $C_2-C_{20}$-alkenyl group, a $C_7-C_{40}$-arylalkyl group, a $C_8-C_{40}$-arylalkenyl group, a $C_7-C_{40}$-alkylaryl group, or $R^8$ and $R^9$ together with the atoms connecting them form a ring, m and n are identical or different and are zero, 1 or 2, where m plus n is zero, 1 or 2, wherein the two indenyl ligands have substitution patterns different from one another on the six-member ring of the indenyl ligands.

2. The process as claimed in claim 1, wherein the metallocene is supported, prepolymerized, or supported and prepolymerized.

3. The process as claimed in claim 1, wherein said cocatalyst is an aluminoxane.

* * * * *